(12) United States Patent
Huang et al.

(10) Patent No.: US 11,503,833 B2
(45) Date of Patent: Nov. 22, 2022

(54) ***BACILLUS THURINGIENSIS* NOVONEST4 AND APPLICATIONS THEREOF**

(71) Applicant: Hubei Biopesticide Engineering Research Center, Hubei (CN)

(72) Inventors: Daye Huang, Hubei (CN); Chunxia Cao, Hubei (CN); Jingwu Yao, Hubei (CN); Yani Zhang, Hubei (CN); Xianqing Liao, Hubei (CN); Fang Liu, Hubei (CN); Ben Rao, Hubei (CN); Ronghua Zhou, Hubei (CN)

(73) Assignee: Hubei Biopesticide Engineering Research Center, Wuhan (CN)

( * ) Notice: Subject to any disclaimer, the term of this patent is extended or adjusted under 35 U.S.C. 154(b) by 19 days.

(21) Appl. No.: 17/039,435

(22) Filed: Sep. 30, 2020

(65) Prior Publication Data

US 2021/0022347 A1 Jan. 28, 2021

Related U.S. Application Data

(63) Continuation of application No. PCT/CN2019/120719, filed on Nov. 25, 2019.

(30) Foreign Application Priority Data

Apr. 12, 2019 (CN) .......................... 201910293167.4

(51) Int. Cl.
*A01N 63/23* (2020.01)
*C12N 1/20* (2006.01)
*C12R 1/07* (2006.01)

(52) U.S. Cl.
CPC ............. *A01N 63/23* (2020.01); *C12N 1/205* (2021.05); *C12R 2001/075* (2021.05)

(58) Field of Classification Search
CPC ... A01N 63/23; C12N 1/205; C12R 2001/075
USPC ...................................................... 424/93.461
See application file for complete search history.

(56) References Cited

FOREIGN PATENT DOCUMENTS

| CN | 1715396 | A | | 1/2006 |
| CN | 103695362 | A | | 4/2014 |
| CN | 103923204 | A | | 7/2014 |
| CN | 104140941 | A | | 11/2014 |
| CN | 103695362 | | * | 9/2015 |
| CN | 109006078 | A | | 12/2018 |
| WO | WO 2016/038067 | A1 | | 3/2016 |

OTHER PUBLICATIONS

Daye Huang et al., "Studies on Controlling Effect of Bacillus thuringiensis NBIN863 Strain on Tomato Root Knot Nematodes and Its Growth-promoting Effect on Tomato," China Vegetables, 2015(10), pp. 57-60 (2005).
Peng, Qi, et al., "Research Prospects in Insecticidal Crystal Proteins of *Bacillus thuringiensis*," Chinese Journal of Biological Control, vol. 31(5), pp. 712-722 (Oct. 2015).

* cited by examiner

*Primary Examiner* — Jennifer M. H. Tichy
(74) *Attorney, Agent, or Firm* — Mei & Mark LLP; Manni Li

(57) ABSTRACT

Strain of *Bacillus thuringiensis* novonest4 and applications thereof. The *Bacillus thuringiensis* is the *Bacillus thuringiensis* novonest4, with an Accession No. CCTCC NO: M2018443. The strain is firstly reported to have both the effect of preventing and controlling lepidoptera pests after foilar application and the effects of degrading carbendazim, promoting crop growth and increasing crop yield after soil application, and has wide application prospects in agricultural production.

7 Claims, 1 Drawing Sheet

BACILLUS THURINGIENSIS NOVONEST4 AND APPLICATIONS THEREOF

CROSS-REFERENCE TO RELATED APPLICATIONS

The subject application is a continuation of PCT/CN2019/120719 filed on Nov. 25, 2019, which claims priority on Chinese Application No. CN201910293167.4 filed on Apr. 12, 2019 in China. The contents and subject matter of the PCT international application and the Chinese priority application are incorporated herein by reference.

BACKGROUND OF THE INVENTION

Technical Field

The invention belongs to the field of agricultural microorganisms, and discloses a strain of Bacillus thuringiensis novonest4 and applications thereof.

Description of Related Art

The use of chemical pesticides plays a critical role both in preventing and controlling diseases, pests and weeds, and in retrieving crop losses, which greatly increases agricultural productivity and promotes the development of modern agriculture. However, along with the use of the chemical pesticides, problems such as environmental pollution, pesticide residues, and drug resistance have arisen. With the progress of society and the improvement of the living standard of people, there is an urgent need for safer and more effective means of preventing and controlling diseases, pests, and weeds.

Owing to the advantages of high efficiency, low cost, and safety, microbial degradation has become an effective way of disposing of various organic pollutants. In recent years, the microbial degradation of pesticide residue pollution has been broadly concerned. Bioremediation companies have produced degrading microorganisms and preparation products thereof on a large scale. Beijing Jianongxin Trade Development Co., Ltd., in China has successfully produced a biodegradation agent named "Biya," which can be used to remove the residues of organophosphorus pesticides.

Bacillus thuringiensis (Bt for short) is a Gram-positive bacterium, which was first isolated from dead silkworms by Japanese scientists who found that the bacterium can effectively kill some lepidopteran pests. Studies have demonstrated that the Bacillus thuringiensis can produce parasporal crystals, which are also known as insecticidal crystal proteins. The insecticidal proteins produced by the Bacillus thuringiensis can be dissolved under alkaline conditions. After being eaten by target insects, the insecticidal proteins can be degraded into active peptide substances in the alkaline environment inside the insects, and then converted into toxins having broad-spectrum insecticidal activity through chemical degradation or enzymolysis. The insecticidal proteins produced by most Bacillus thuringiensis strains have an obvious toxic effect on lepidoptera insects, and those produced by some strains are also toxic to diptera and coleoptera species. However, not all the Bacillus thuringiensis has a killing effect on the lepidopteran pests, and it is necessary to obtain a strain highly toxic to the target pests through massive screening.

In addition to the activity against the pests above, Bacillus thuringiensis has also been reported as promoting growth, killing nematodes, and degrading pesticides. For example, the inventor once provided a strain of NBIN863, which has the effect of killing tomato root-knot nematodes and promoting growth, but has no effect against lepidopteran pests, and Bt-1 strains have the effect of degrading azoxystrobin, kresoxim-methyl, pyrazole-kresoxim-methyl, beta-cypermethrin, deltamethrin, lambda-cyhalothrin, fenpropathrin, and other pesticides. There have been some reports on carbendazim degrading bacteria, such as Bacillus pumilus strains NY97-1, Rhodococcus jialingiae strains dj1-6-2, and Rhodococcus erythropolis strains XJ-D. It is the first time to report the degradation effect of Bacillus thuringiensis against carbendazim. However, there are many microorganisms having the activity of degrading pesticides, and the use of a single-function microorganism is high in cost. A microorganism having pesticide activity, pesticide-degrading activity, and bacterial-manure growth-promoting properties may significantly improve the utilization of the microorganisms to further increase quality and enhance the effect.

BRIEF SUMMARY OF THE INVENTION

An isolated strain of Bacillus thuringiensis, wherein the Bacillus thuringiensis is Bacillus thuringiensis novonest4, with CCTCC Accession No: M2018443. The deposit of the biological material for the subject application was made at China Center for Type Culture Collection (CCTCC), having an address at Wuhan University, Luojiashan, Wuchang, Wuhan, 430072, China, on Jul. 4, 2018; the deposit has the CCTCC Accession No. M2018443; the deposited biological material is described as Bacillus thuringiensis novonest4; and the deposit has been made under the Budapest Treaty.

Regarding the application of an isolated strain of Bacillus thuringiensis, the strain may be used to prepare microbial preparations with multiple effects including the degradation of carbendazim, the promotion of plant growth, and the prevention and control of lepidopteran pests.

To achieve the object described above, a technical measure employed in the invention is as follows.

An isolated strain of Bacillus thuringiensis was obtained by dual functional screening in terms of the activity of killing lepidopteran pests and the activity of degrading carbendazim. The Bacillus thuringiensis was further identified by combining 16s rDNA and physiological and biochemical identification. This strain was sent to the CCTCC for preservation on Jul. 4, 2018 with a class designated as Bacillus thuringiensis novonest4 and CCTCC Accession No. M2018443.

The colony of the Bacillus thuringiensis was milky white and grew well in the NA medium, and spores and parasporal crystals were observed under microscopic examination.

The application of an isolated strain of Bacillus thuringiensis includes preparing a crop microbial preparation using the Bacillus thuringiensis. The preparation has the effects of degrading carbendazim, promoting crop growth, and preventing and controlling lepidopteran pests at the same time.

In the application described above, preferably, the crops refer to tea, Codonopsis pilosula, Magnolia officinalis, Atractylodes macrocephala, Coptis chinensis, rice, corn, wheat, soybean, tomato, cabbage, pepper or cucumber.

In the application described above, preferably, the lepidopteran pests refer to tea geometrids, tea tussock moths, corn borers, rice stem borers, diamond back moths, tea budworms or Spodoptera litura.

Compared with the prior art, the invention has the following advantages.

(1) The invention provides a strain of Bacillus thuringiensis, which is highly resistant to stress and easy to ferment in bulk, and reports on its degradation activity against carbendazim are offered for the first time, showing an important application value.

(2) The strain has both insecticidal and growth-promoting activities, is easy to use, and has no residue or pollution, whereby the application of chemical fertilizers and pesticides can be reduced effectively.

BRIEF DESCRIPTION OF THE SEVERAL VIEWS OF THE DRAWINGS

FIG. 2A shows the effect of novonest 4; and FIG. 2B shows the effect of Fresh water.

DETAILED DESCRIPTION OF THE INVENTION

The present invention is described in details in the following examples, and the examples do not limit the scope of the inventoin. The reagents or materials are sourced from commercial channels and techniques are conventionally known, unless otherwise specified.

Example 1

Production and Identification of *Bacillus thuringiensis* Novonest4

The *Bacillus thuringiensis* novonest4 was sourced from the *Bacillus thuringiensis* Resource Library of Hubei Biopesticide Engineering Research Center, and was simultaneously screened for the activity of killing lepidopteran pests and the activity of degrading carbendazim to obtain a dual-effect strain. The strain was further identified in its classification status by combining 16s rDNA and physiological and biochemical identification (Table 1, Table 2), and then was sent to the CCTCC for preservation, with a class designated as *Bacillus thuringiensis* novonest4 and the CCTCC Accession No. M2018443.

In the invention, *Bacillus thuringiensis* novonest4 is alternatively abbreviated as novonest4.

Figure 1:
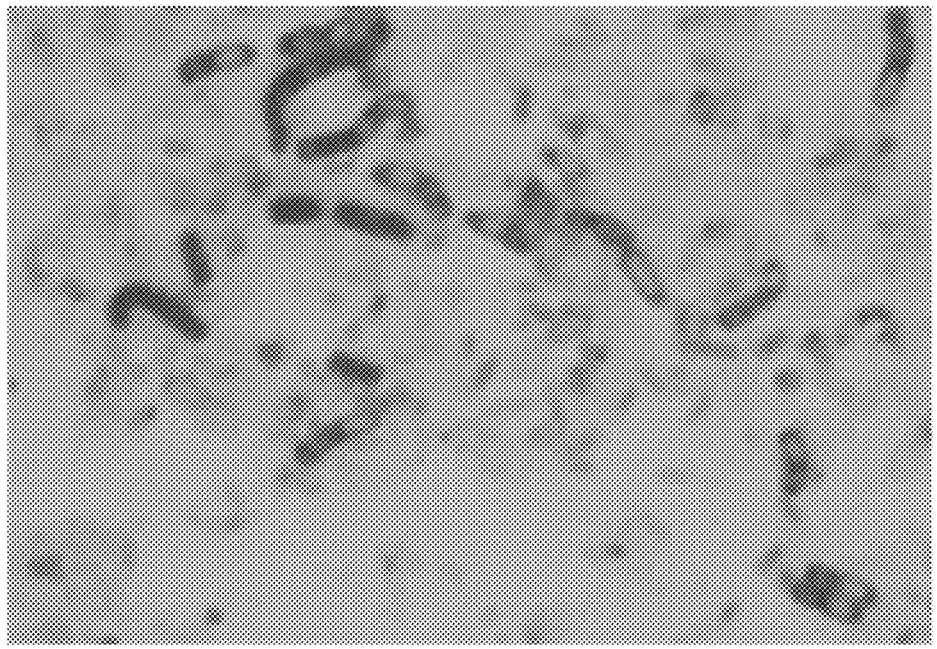
FIG. 1 is a microphotograph (1000×) showing the *Bacillus thuringiensis* novonest4 of the present invention.

The colony of the *Bacillus thuringiensis* was milky white and grew well in the NA medium, and spores and parasporal crystals were observed under microscopic examination as shown in FIG. 1.

TABLE 1

Physiological-biochemical characteristics of *Bacillus thuringiensis* novonest4: enzyme activity and carbon-source oxidation

| | Substrates and Enzymes for Reaction | | Test Results |
|---|---|---|---|
| ONPG | o-nitrobenzene-galactoside | β-galactosidase | − |
| ADH | Arginine | Arginine dihydrolase | + |
| LDC | Lysine | Lysine decarboxylase | − |
| ODC | Ornithine | Ornithine decarboxylase | − |
| CIT | Sodium Citrate | Citrate Utilization | − |
| H2S | Sodium thiosulfate | Generation of H2S | + |
| URE | Urea | Urease | − |
| TDA | Tryptophan | Tryptophan deaminase | + |
| IND | Tryptophan | Generation of Indole | − |
| VP | Pyruvate | 3-hydroxybutanone produced acetylmethylcarbinol | + |

TABLE 1-continued

Physiological-biochemical characteristics of *Bacillus thuringiensis* novonest4: enzyme activity and carbon-source oxidation

| | Substrates and Enzymes for Reaction | | Test Results |
|---|---|---|---|
| GEL | Kohn gelatin | Gelatinase | + |
| GLU | Glucose | Fermentation/Oxidation (4) | + |
| MAN | Mannitol | Fermentation/Oxidation (4) | − |
| INO | Inositol | Fermentation/Oxidation (4) | − |
| SOR | Sorbitol | Fermentation/Oxidation (4) | − |
| RHA | Rhamnose | Fermentation/Oxidation (4) | − |
| SAC | Saccharose | Fermentation/Oxidation (4) | − |
| MEL | Melibiose | Fermentation/Oxidation (4) | − |
| AMY | Amygdalin | Fermentation/Oxidation (4) | − |
| ARA | Arabinose | Fermentation/Oxidation (4) | − |

+: positive reaction; +: negative reaction

TABLE 2

Physiological-biochemical characteristics of *Bacillus thuringiensis* novonest4: acid production with a carbon source

| Tube/Substrate Corresponding to Reagent Strip | Test Result | Tube/Substrate Corresponding to Reagent Strip | Test Results |
|---|---|---|---|
| 0 Control | − | Esculin | + |
| 1 Glycerinum | − | 26 Salicin | − |
| 2 Erythritol | − | 27 Cellobiose | + |
| 3 D-Aarabinose | − | 28 Maltose | + |
| 4 L-Aarabinose | − | 29 Lactose | − |
| 5 Ribose | + | 30 Melibiose | − |
| 6 D-Xylose | − | 31 Sucrose | + |
| 7 L-Xylose | − | 32 Trehalose | + |
| 8 Adonitol | − | 33 Inulin | − |
| 9 β-methyl-D-xyloside | − | 34 Melezitose | − |
| 10 Galactose | − | 35 Raffinose | − |
| 11 Glucose | + | 36 Starch | + |
| 12 Fructose | + | 37 Glycogen | + |
| 13 Mannose | + | 38 Xylitol | − |
| 14 Sorbose | − | 39 Geraniol | − |
| 15 Rhamnose | − | 40 D-turanose | − |
| 16 Dulcitol | − | 41 D-lyxose | − |
| 17 Inositol | − | 42 D-tagatose | − |
| 18 mannitol | − | 43 D-fucose | − |
| 19 Sorbitol | − | 44 L-fucose | − |
| 20 α-methyl-D-mannoside | − | 45 D-arabitol | − |
| 21 α-methyl-D-glucoside | − | 46 L-arabitol | − |
| 22 N-acetyl-glucosamine | + | 47 Gluconate | − |
| 23 Amygdalin | − | 48 2-keto-gluconate | − |
| 24 Arbutin | − | 49 5-keto-gluconate | − |

+: positive reaction; +: negative reaction;

Example 2

Fermentation of *Bacillus thuringiensis* Novonest4

(1) Primary seed culture: 200 ml of primary seed medium was added to a 500 ml Erlenmeyer flask, and sterilized with moist heat at 120° C. for 15-30 min, and then, a freeze-dried tubed strain of live *Bacillus thuringiensis* was taken and inoculated into the primary seed medium, and then incubated at 35° C. for 10 h.

The medium used for the primary seed culture included: 1% of glucose (g/L, the same below), 2% of beef extract, 1% of peptone, and 0.5% of sodium chloride, with a pH of 7.

(2) Secondary seed culture: 150 L of secondary seed medium was added to a 400 L fermentor, and sterilized with moist heat at 120° C. for 30 min. 200 ml of primary seeds were inoculated into the secondary seed medium, and incubated at 35° C. for 10 h, with a controlled fermentor pressure of 0.05 Mpa, a stirring speed of 120 rpm, and a ventilation ratio of 1:1.0.

The medium used for the secondary seed culture included: 2% of glucose, 1% of yeast extract, 2% of peptone, 0.05% of dipotassium hydrogen phosphate, 1% of sodium chloride, and 0.05% of magnesium sulfate. The pH of the medium was adjusted to 7.

(3) Fermentation: 25 m3 of live *Bacillus thuringiensis* fermentation medium was added to a 40 m3 fermentor, and sterilized with moist heat at 120° C. for 30 minutes. 200 L of secondary seeds were inoculated into the live *Bacillus thuringiensis* fermentation medium, and incubated at 35° C. for 36 h, with a controlled fermentor pressure of 0.04 Mpa, a stirring speed of 100 rpm, and a ventilation ratio of 1:0.5.

The raw materials and amount of the medium used for the fermentation included: 1% of corn starch, 2% of peanut cake powder, 1% of fish meal, 0.5% of yeast extract powder, 0.5% of peptone, 0.05% of potassium dihydrogen phosphate, and 0.05% of magnesium sulfate, with a pH of pH7.

(4) The fermentation was ended when 40% of the spores and crystals were separated. After counting, the spores had a count of $5 \times 10^9$ cfu/mL, and were used as a fermentation stock solution for the following embodiments.

Example 3

Figure 2A:
FIGS. 2A and 2B show the effect of *Bacillus thuringiensis* novonest4 of the present invention on preventing and controlling tea geometrids, where
Figure 2B:

Insecticidal Activity of *Bacillus thuringiensis* Novonest4 Against Tea Geometrids The fermentation stock solution of *Bacillus thuringiensis* novonest4 prepared in Embodiment 2 was tested by a leaf soaking and feeding method. That is, 100-fold and 200-fold Bt solutions were prepared from sterile water, fresh water was used as a control, and the test was conducted in triplicate. Tea leaves were soaked for 10 min, removed, air-dried, and then fed to newly-hatched larvae of the tea geometrid. Laboratory tests shown that the *Bacillus thuringiensis* novonest4 diluted to 100 fold and 200 fold exhibited good prevention and control effect on the tea geometrids (FIGS. 2A and 2B). FIG. 2A shows diseased blades after 5 days after a 100-fold diluted solution of the microbial preparation of the invention is added, and FIG. 2B shows diseased blades after water is added as a control. As can be seen from FIGS. 2A and 2B and Table 3, the 100-fold diluted solution shows 100% of a protecting force for the blades. Statistics were conducted after 2d, 3d, 4d, and 5d. Each treatment was conducted in an artificial incubator at 25° C. with a relative humidity of 80% and a luminance of 2000 lx. Based on regular examinations every day, the number of deaths of test larvae were noted.

TABLE 3

Control effect of *Bacillus thuringiensis* novonest4 against tea geometrids

| Treatment | 2D after Application Control Effect (%) | 3D after Application Control effect (%) | 4D after Application Control effect (%) | 5D after Application Control effect (%) |
|---|---|---|---|---|
| 100-fold diluted solution of *Bacillus thuringiensis* | 89.30 | 94.43 | 100 | 100 |
| 200-fold diluted | 48.60 | 51.67 | 75.54 | 70.64 |

TABLE 3-continued

Control effect of *Bacillus thuringiensis* novonest4 against tea geometrids

| Treatment | 2D after Application Control Effect (%) | 3D after Application Control effect (%) | 4D after Application Control effect (%) | 5D after Application Control effect (%) |
|---|---|---|---|---|
| solution of *Bacillus thuringiensis* | | | | |
| Fresh water | — | — | — | — |

Due to space limitations, the insecticidal activity data of the *Bacillus thuringiensis* novonest4 on the tea geometrids were only recorded in the text of this application. During actual testing, the strain also shown good effect on killing tea tussock moths, corn borers, rice stem borers, diamond back moths, tea budworms, or Spodoptera litura.

Example 4

Degradation Effect of *Bacillus thuringiensis* Novonest4 Against Carbendazim (1) A basic medium having a volume of 180 ml (500 ml Erlenmeyer flask) was added with 80 mg of 50% carbendazim wettable powder, and then added with 20 ml of the BT fermentation stock solution prepared in Embodiment 2, with BT sterile water as a control. Both were incubated on a shaker (170 rpm/min) at 30° C. After 7 days, samples was taken for measurement. The control and 5 ml of a treated basic medium suspension were transferred into a 50 ml separating funnel, and extracted three times with 10 ml of dichloromethane. A lower organic phase passed through anhydrous sodium sulfate and was combined in a 250 ml round-bottom flask. The round-bottom flask was then placed on a rotary evaporator for reduced-pressure concentration to near-dryness, and then a resulting product was blown with nitrogen to dryness. Methanol was added to reach 10 ml, and HPLC was performed for testing.

The formula of the basic medium was: 1.0 g of NH4NO3, 1.5 go of K2HPO4, 0.5 g of $KH_2PO_4$, 0.2 g of $MgSO_4$, 0.5 g of NaCl, and the balance of water, which was added to reach 1 L.

(2) 1000 g (dry weight) of soil to which carbendazim was not applied was weighed, added with carbendazim to allow the carbendazim to reach a concentration of 50 mg/kg, and then added with the novonest4 fermentation solution to allow the novonest4 to reach a concentration of $10^8$ spores per 1 g of soil. They were placed in an incubator at 30° C. and incubated in a dark condition at constant temperature. After 10 days, sampling was performed to determine the residual amount of the carbendazim in the soil. The results are shown in Table 4, where the degradation rate against the carbendazim was 53.45% in a shake flask, and reached 35.40% in soil.

TABLE 4

Degradation rate of *Bacillus thuringiensis* novonest4 against Carbendazim

| Medium | Inorganic salt medium | Soil |
|---|---|---|
| Degradation rate | 53.45% | 35.40% |

Example 5

Growth-Promoting Effect of *Bacillus thuringiensis* novonest4 on Tea

The tests were carried out in August 2018 in the tea garden of Yingshan County, Huanggang, Hubei, at an altitude of 107 meters. After the tea harvesting in summer, the novonest4 fermentation solution at a level of $5\times10^9$ cfu/mL was sprayed on the roots of the tea trees at the use level of 20 L/mu. Those without the spraying of the BT fermentation solution were taken as a control. In October 2018, the budding density and the weight of one bud and two leaves were counted. With the application of the novonest4, an obvious growth-promoting effect was achieved on the tea, with the budding density increased by 26.34%, and the weight of one-hundred buds increased by 22.86% as shown in Table 5.

TABLE 5

Growth-promoting Effect of *Bacillus thuringiensis* novonest4 on Tea

| Treatment | Budding density (0.1 m$^2$) | Hundred-bud Weight (g) |
|---|---|---|
| *Bacillus thuringiensis* novonest4 | 101.7 | 38.48 |
| CK | 80.5 | 31.32 |

Due to space limitations, the growth-promoting effect data of the *Bacillus thuringiensis novonest*4 on the tea were only recorded in the text of this application. During actual testing, this strain also has a growth-promoting effect on tea, rice, corn, wheat, soybean, tomato, cabbage, pepper, cucumber and traditional herbal medicines such as *Codonopsis pilosula, Magnolia officinalis, Atractylodes macrocephala* and *Coptis chinensis*.

We claim:

1. A method for degrading carbendazim, comprising:
   incubating a strain of *Bacillus thuringiensis* to obtain a seed culture, wherein the strain of *Bacillus thuringiensis* is *Bacillus thuringiensis* novonest4 with CCTCC Accession No. M2018443,
   incubating the seed culture to obtain a fermentation stock solution, wherein the fermentation stock solution comprises spores and parasporal crystals of the strain of *Bacillus thuringiensis*,
   treating a system containing carbendazim with the fermentation stock solution and degrading the carbendazim in the system.

2. The method of claim 1, wherein the fermentation stock solution comprises the spores at a count of $5\times10^9$ cfu/mL or more.

3. The method of claim 1, wherein at least 40% of the spores and the parasporal crystals are separated in the fermentation stock solution.

4. The method of claim 1, further comprising
   incubating the strain of *Bacillus thuringiensis* in a primary seed culture medium to obtain a primary seed culture,
   incubating the primary seed culture in a secondary seed culture medium to obtain a secondary seed culture, and
   incubating the secondary seed culture in a fermentation medium to obtain the fermentation stock solution.

5. The method of claim 1, wherein the system containing carbendazim is soil.

6. The method of claim 5, wherein the fermentation stock solution is at a concentration of $10^8$ spores per 1 g of soil or more for treating the soil containing carbendazim.

7. The method of claim 1, wherein the system containing carbendazim is treated with the fermentation stock solution at 30° C.

\* \* \* \* \*